United States Patent
Brady et al.

(10) Patent No.: US 11,957,839 B2
(45) Date of Patent: *Apr. 16, 2024

(54) INTUBATION ASSEMBLY TO PROTECT FROM AIRBORNE ILLNESSES

(71) Applicant: SafER Medical Products, LLC, Branson, MO (US)

(72) Inventors: Rob Brady, Sarasota, FL (US); Matt Vergin, St. Petersburg, FL (US); Barry Jennings, Largo, FL (US); Steve MacFarlane, Bradenton, FL (US); Richard Blubaugh, Branson West, MO (US); Craig Randall, Branson, MO (US); Misty Denevan, Branson, MO (US); Todd Baker, Walnut Shade, MO (US)

(73) Assignee: Safer Medical Products, LLC, Branson, MO (US)

(*) Notice: Subject to any disclaimer, the term of this patent is extended or adjusted under 35 U.S.C. 154(b) by 436 days.

This patent is subject to a terminal disclaimer.

(21) Appl. No.: 17/177,432

(22) Filed: Feb. 17, 2021

(65) Prior Publication Data

US 2022/0072251 A1 Mar. 10, 2022

Related U.S. Application Data

(60) Provisional application No. 63/075,862, filed on Sep. 9, 2020.

(51) Int. Cl.
*A61M 16/04* (2006.01)
*A61M 16/00* (2006.01)

(52) U.S. Cl.
CPC ...... *A61M 16/047* (2013.01); *A61M 16/0003* (2014.02); *A61M 16/049* (2014.02)

(58) Field of Classification Search
CPC ....... A61M 16/00–0003; A61M 16/0087–009; A61M 16/04–0655; A61M 2016/0661; A61B 90/05
See application file for complete search history.

(56) References Cited

U.S. PATENT DOCUMENTS

| | | |
|---|---|---|
| 5,370,110 A | 12/1994 | Corn |
| 5,676,133 A | 10/1997 | Hickle |

(Continued)

FOREIGN PATENT DOCUMENTS

| | | |
|---|---|---|
| CN | 105797246 A | 7/2016 |
| CN | 206007759 U | 3/2017 |

(Continued)

OTHER PUBLICATIONS

International Search Report and Written Opinion of PCT/US2021/048145; United States Patent Office; dated Dec. 9, 2021; entire document.

(Continued)

*Primary Examiner* — Rachel T Sippel
(74) *Attorney, Agent, or Firm* — Allen, Dyer, Doppelt & Gilchrist, P.A.

(57) ABSTRACT

An intubation assembly and shield configured to at least partially reduce the risk of contagion of airborne illnesses. The intubation assembly comprises an intubation apparatus assembly, which may comprise an intubation apparatus such as a laryngoscope, endoscope, bronchoscope, or other fiberoptic device. The intubation apparatus assembly may be operatively disposed on the shield assembly. The intubation apparatus may be placed on a correspondingly dimensioned sleeve. The shield assembly comprises a body with a plurality of side segments and a first transparent component with a shield opening disposed thereon. The shield opening may be used for insertion of the intubation apparatus assembly. The shield assembly may also comprise a second (Continued)

transparent component with at least one longitudinally disposed slot for insertion of an endotracheal tube or other intubation apparatus(es). The shield assembly may be provided with ports to attach a vacuum device to provide negative pressure.

24 Claims, 13 Drawing Sheets

(56) References Cited

U.S. PATENT DOCUMENTS

| | | |
|---|---|---|
| 11,049,626 B1 * | 6/2021 | Ahearn .................. A61B 90/05 |
| 2002/0045796 A1 | 4/2002 | O'Connor et al. |
| 2009/0020128 A1 | 1/2009 | Metzger et al. |
| 2014/0338677 A1 | 11/2014 | Sparkuhl |
| 2016/0074268 A1 | 3/2016 | Breegi et al. |
| 2016/0107006 A1 | 4/2016 | Giulianotti et al. |
| 2016/0136024 A1 | 5/2016 | Poenisch et al. |
| 2021/0307872 A1 | 10/2021 | Vizulis et al. |
| 2021/0346624 A1 | 11/2021 | Fiorenza |
| 2022/0015860 A1 * | 1/2022 | Luk ........................ A61B 90/40 |
| 2022/0355052 A1 * | 11/2022 | Alonso Babarro ......................... A61B 1/00048 |

FOREIGN PATENT DOCUMENTS

| | | |
|---|---|---|
| WO | WO1995033506 | 12/1995 |
| WO | WO2021207292 | 10/2021 |

OTHER PUBLICATIONS

International Search Report and Written Opinion for PCT/US2021/049619; dated Feb. 28, 2022; ISA—United States Patent and Trademark Office; entire document.

Sovereign Medical, Inc.; Exhlo Shield; Product Information Sheet; Online; Apr. 3, 2020; entire document; https://sovmed.com/wp-content/uploads/2020/07/EXHALO-Introduction-Summary-Soverign-Medical-ed3.pdf.

* cited by examiner

INTUBATION ASSEMBLY TO PROTECT FROM AIRBORNE ILLNESSES

FIELD OF INVENTION

The present invention relates to protective shields for intubation, endoscope, bronchoscope, or other procedures that may generate aerosol or respiratory pathogens.

BACKGROUND

The spread of airborne illnesses poses a serious health risk, not only to individuals within the community, but also to health practitioners. This is relevant to patients that have contracted an airborne illness, for example a respiratory illness such as influenza, and more recently COVID-19. Such ill patients may require health practitioners to perform a procedure, for example an intubation, endoscopy, bronchoscopy, or other procedures, especially those requiring fiberoptic devices. During the process of performing the procedure, the health practitioners may be at risk of contagion of the airborne illness. Thus, a benefit would be realized by providing an intubation assembly that can act as a shield to cover the face of an ill patient. It would be ideal if such an intubation assembly would allow a health practitioner to insert a laryngoscope, endoscope, bronchoscope, or other fiberoptic device through the shield. Another benefit would also be realized if the intubation assembly would also allow the health practitioner to insert an endotracheal tube through the shield. An even further benefit would be realized if the shield comprised a substantially transparent material that would permit visibility of the patient and the intubation area. Yet a further benefit would be realized if such an intubation assembly would be provided with various operative components that would capable of being connected to a vacuum system to provide for a negative pressure that may at least partially removed exhaled air from the patient.

SUMMARY

The present invention relates to an intubation assembly and shield assembly that may at least partially reduce the risk of contagion of airborne illnesses, including from a patient to healthcare personnel, i.e., physician, nurse, assistant, etc. The present invention also relates to a method of using the inventive intubation assembly. The intubation assembly and shield assembly according to the present invention at least partially reduces exposure of healthcare personnel and others to exhaled infectious particles such as viruses and bacteria. The intubation assembly and shield assembly according to the present invention at least partially allows for protection against exhaled infectious particles. Further, the intubation assembly and shield assembly according to the present invention may at least partially provide a seal between the laryngoscope, endoscope, bronchoscope, or other fiberoptic device and the patient at the location where it is fitted and/or inserted. Furthermore, the intubation assembly and shield assembly according to the present invention may also at least partially provide a seal at the area where the endotracheal tube is inserted or otherwise passed through. Such a configuration of the intubation assembly and shield assembly, including in the geometry of a shield body, may substantially define an operable arrangement in conjunction with negative pressure vacuums. As such, the intubation assembly and shield assembly according to the present invention, when disposed in such operable arrangement, may at least partially remove the patient's exhaled air. This in turn, may protect the healthcare personnel involved in the procedure by at least partially reducing exposure to exhaled infectious particles.

The intubation assembly comprises an intubation apparatus assembly and a shield assembly. The intubation apparatus assembly may be operatively disposed on a shield assembly. The shield assembly is generally connected to a negative pressure vacuum or otherwise vacuum system. The intubation apparatus assembly may comprise an intubation apparatus, including, but not necessarily limited to a laryngoscope, endoscope, bronchoscope, or other fiberoptic apparatus. The intubation apparatus may be placed on a correspondingly dimensioned sleeve of the intubation apparatus assembly. The sleeve should comprise a geometry such that a health practitioner should be able to hold it with a hand(s). The shield assembly comprises a body with a plurality of side segments. The shield assembly may also comprise a first transparent component with a shield opening disposed thereon. The shield opening may be used for insertion of the laryngoscope assembly. By way of example, the first transparent component may comprise a clear silicone sheet with an opening disposed thereon. The shield assembly may also comprise a second transparent component with at least one longitudinally disposed slot for insertion of an endotracheal tube, and in some embodiments, an endoscope, bronchoscope, or other fiberoptic apparatus.

DETAILED DESCRIPTION

Figure 11:
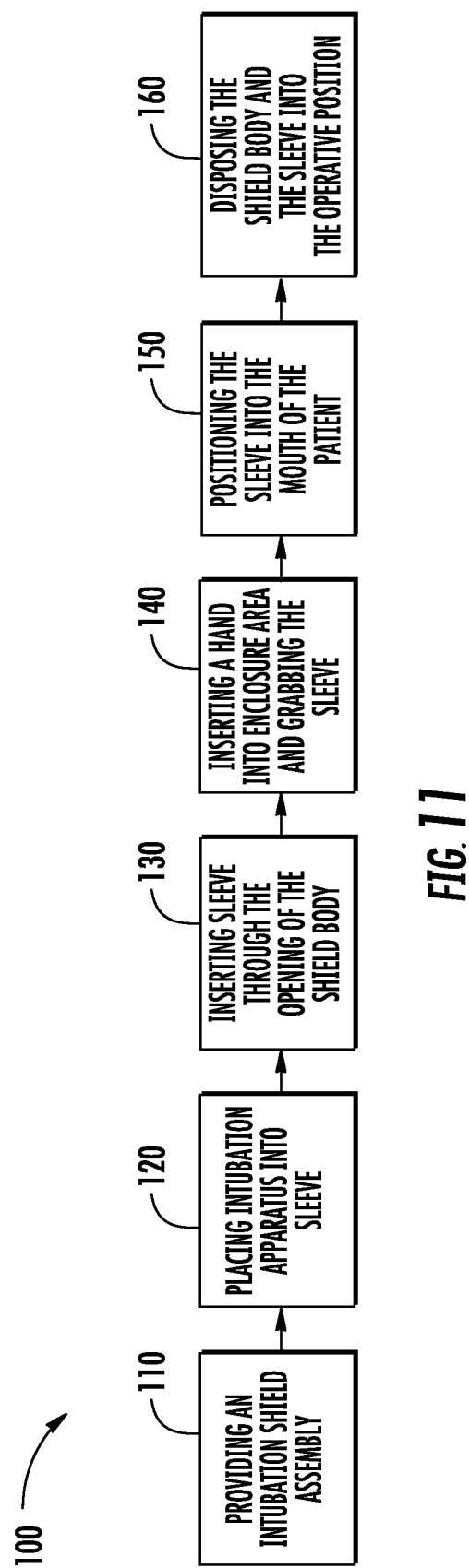
FIG. 11 is a diagrammatic representation of one embodiment of the method of using the intubation assembly according to the present invention.

With initial reference to at least FIGS. 1A-1D, the present invention relates to an intubation assembly, which is indicated at 1. With reference to at least FIG. 3, the present invention is also directed to a shield assembly 20. With reference to FIG. 11, the present invention is further directed to a method 100 of using the intubation assembly 1. It is within the scope of the present invention that the intubation assembly 1 and/or shield 20, using a negative pressure vacuum, at least partially reduce the risk of contagion of airborne illnesses, including from a patient to a health practitioner, i.e., physician, nurse, assistant, etc. That is, the intubation assembly 1 and/or shield 20 may act as a physical barrier that may at least partially reduce airborne movement of infectious particles, including but not necessarily limited to viruses, e.g., influenza or COVID-19, or bacteria, fungi, etc. The intubation assembly 1 and/or shield 20 may also at least partially reduce the risk of contagion of airborne illnesses from the health practitioner to the patient. The intubation assembly 1 generally comprises an intubation apparatus assembly 10 and a shield assembly 20. The intubation apparatus assembly 10 may be operatively disposed on a shield assembly 20. With reference to at least FIG. 2, it is within the scope of the present invention that the intubation assembly 1 and/or shield 20 be used with an intubation apparatus. As used herein, an "intubation apparatus" may include, without limitation, laryngoscopes, endoscopes, bronchoscopes, and other fiberoptic devices. As also used herein, an "intubation apparatus" may also refer to an endoscope assembly, or other related apparatus, as may be used, without limitation, in connection with an upper gastro intestinal (GI) endoscopy (EGD) or similar procedure. Furthermore, it is also contemplated that the inventive intubation assembly 1 be disposable. However, this is not strictly necessary as the inventive intubation assembly 1 may also be disinfected so that it may be used more than once.

Figure 2:
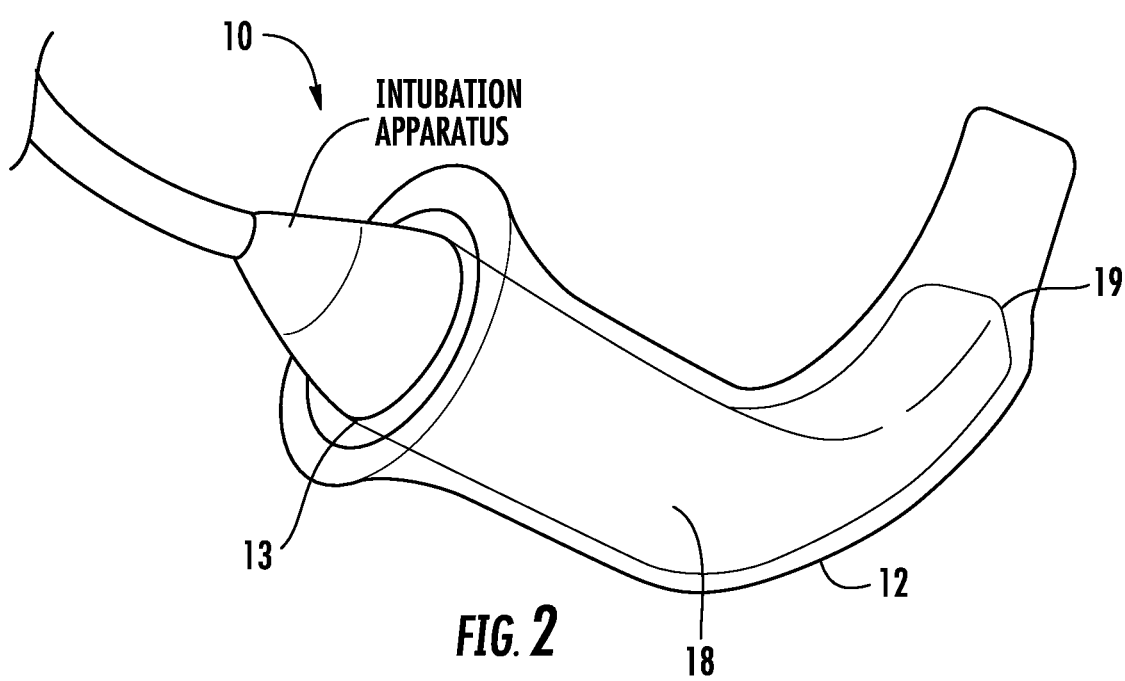
FIG. 2 is a perspective view of one embodiment of the laryngoscope assembly of the intubation assembly according to the present invention.

As is shown at least in FIG. 2, and as mentioned above, the inventive intubation assembly 1 comprises an intubation apparatus assembly 10. The intubation apparatus assembly 10 comprises an intubation apparatus, which may be disposed on a sleeve 12. The sleeve 12 is generally dimensioned to accommodate the size and/or length of the body 18 of the intubation apparatus. It is within the scope of the present invention that the sleeve 12 comprise a material that may create sufficient frictional resistance to engage the intubation apparatus once it is inserted inside of the sleeve 12. The sleeve 12 should also comprise a material that is sufficiently flexible and that may conform to the geometry of the intubation apparatus. It is also contemplated that the material of the sleeve 12 also permit a manual insertion of the intubation apparatus through a sleeve opening 13.

With reference to at least FIGS. 1B and 2, it is also contemplated that the size and geometry of the intubation apparatus assembly 10, including the intubation apparatus and/or sleeve 12, be configured and dimensioned to permit a health practitioner to hold it with a hand(s) after insertion onto the shield assembly 20, which will be described below. As shown at least in FIG. 1B, the sleeve 12 may comprise an elongated and/or curved profile. In the illustrative embodiment of FIG. 2, the sleeve 12 may comprise a substantially square opening, including with rounded corners. Alternatively, as shown at least in FIG. 2 the sleeve 12 may comprise a substantially circular opening 13 at one of its ends. With reference again to FIG. 1B, it is contemplated that the opening 13 of the sleeve 12 be sufficiently large to accommodate insertion of an intubation apparatus. Furthermore, in embodiments comprising a substantially rectangular opening, it is contemplated that the size and configuration of the shield opening 22 be configured and dimensioned accordingly to permit insertion of the sleeve 12 into the shield body 24. Similarly, in embodiments comprising a substantially cylindrical configuration, it is contemplated that the size of the opening 13 of the sleeve 12 comprise a diameter that is at least larger than the diameter of the shield opening 22, which will also be described in more detail below. Furthermore, the sleeve 12 may also comprise a tapered configuration, which may allow the health practitioner to insert it into the mouth, larynx, esophagus, and/or trachea of the patient. As is also appreciated in FIG. 2, the laryngoscope may also comprise an audiovisual component 19. For example, the audiovisual component 19 may comprise a camera.

Figure 1A:
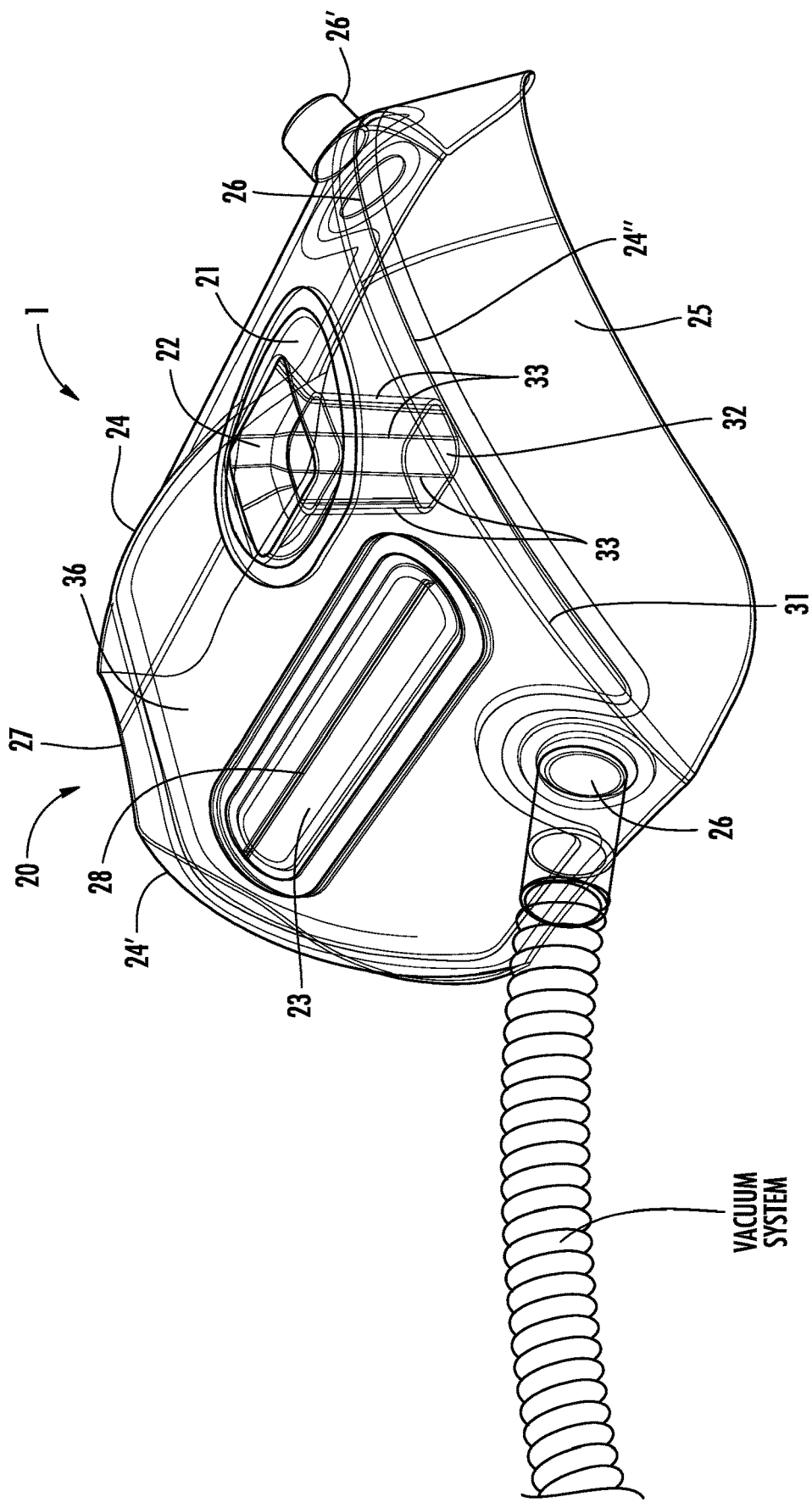
FIG. 1A is a perspective view of one embodiment of the intubation assembly according to the present invention.
Figure 1B:
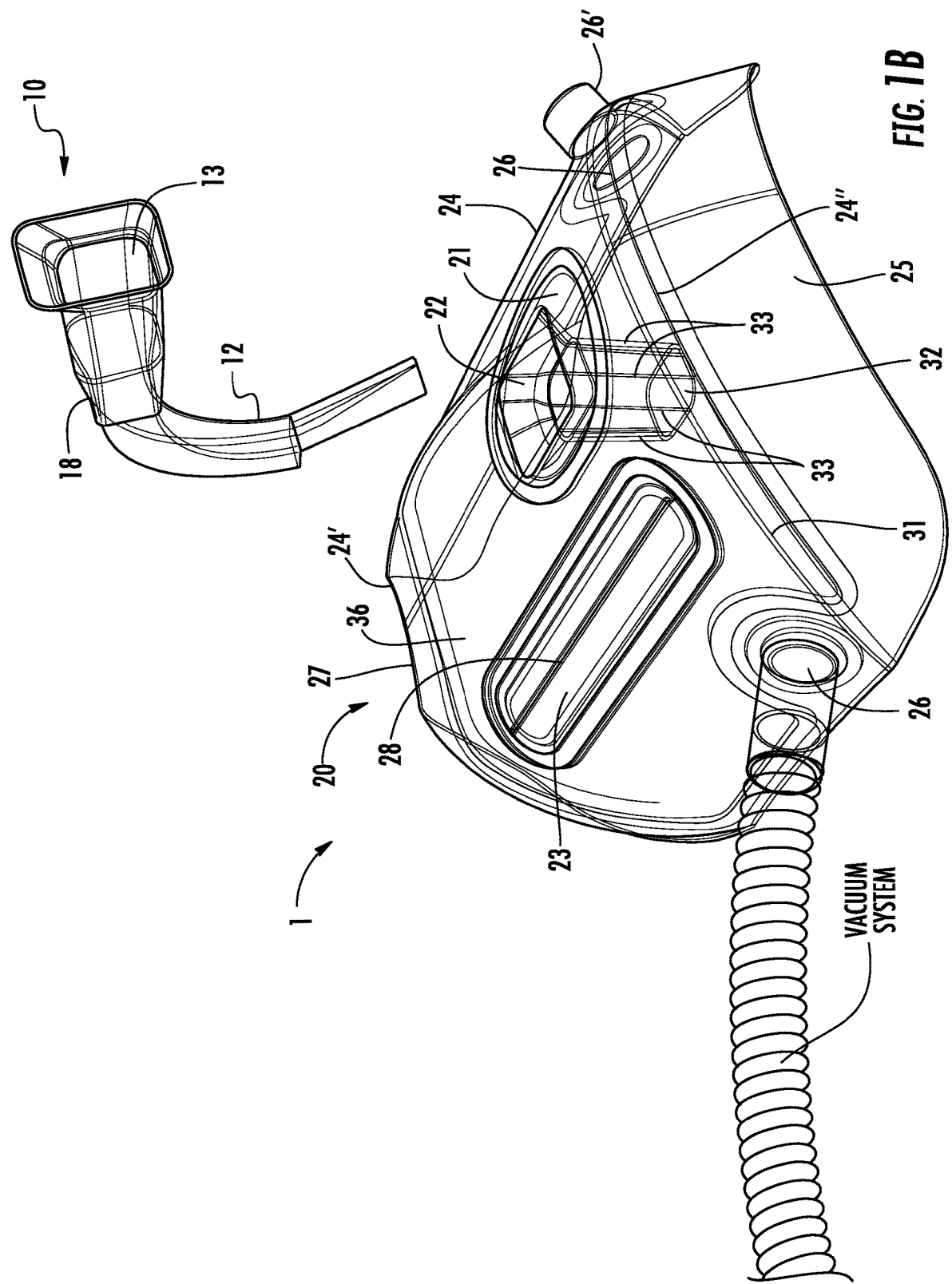
FIG. 1B is a perspective view of another embodiment of the intubation assembly according to the present invention.
Figure 1C:
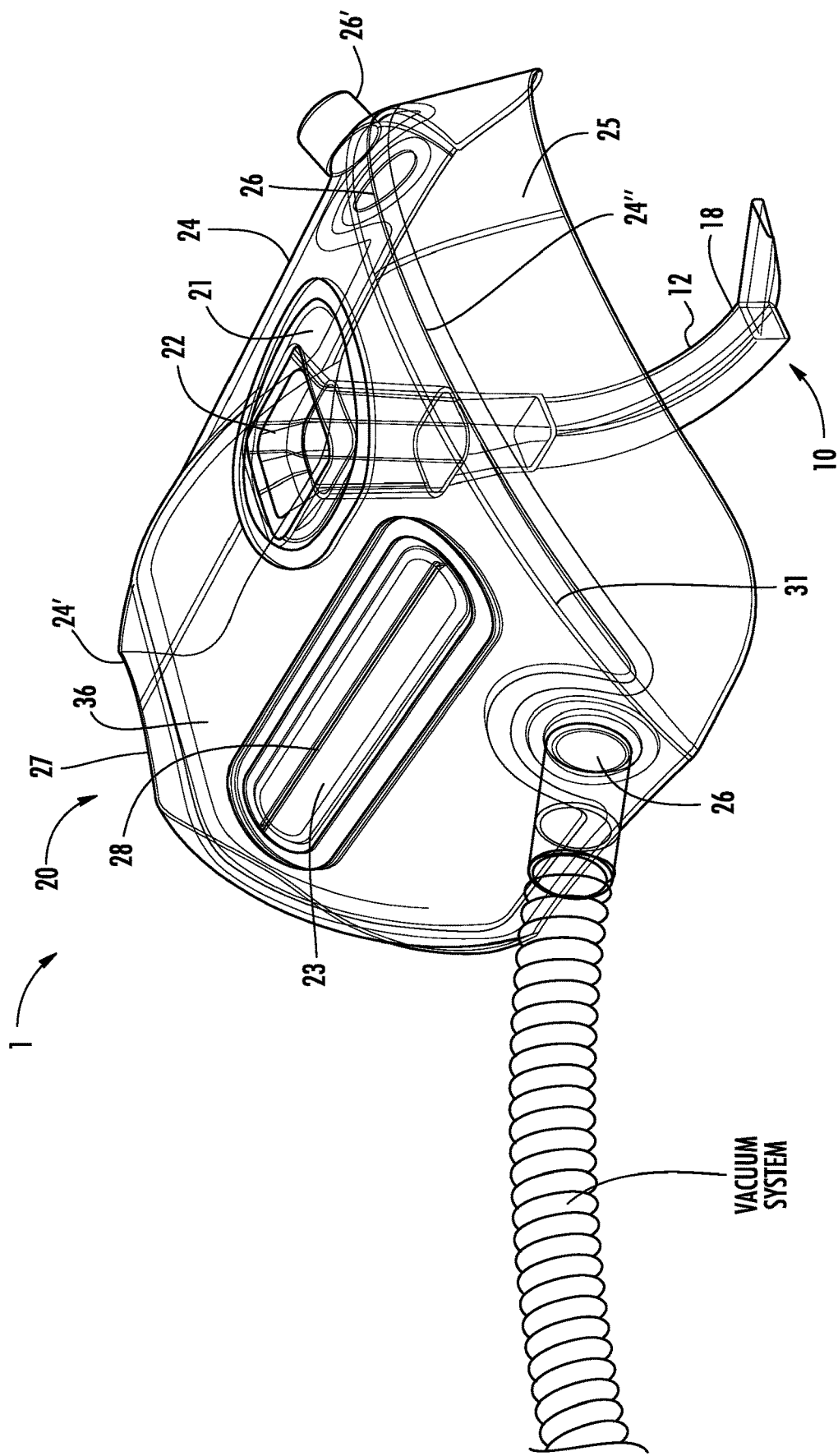
FIG. 1C is a perspective view of yet another embodiment of the intubation assembly according to the present invention.
Figure 1D:
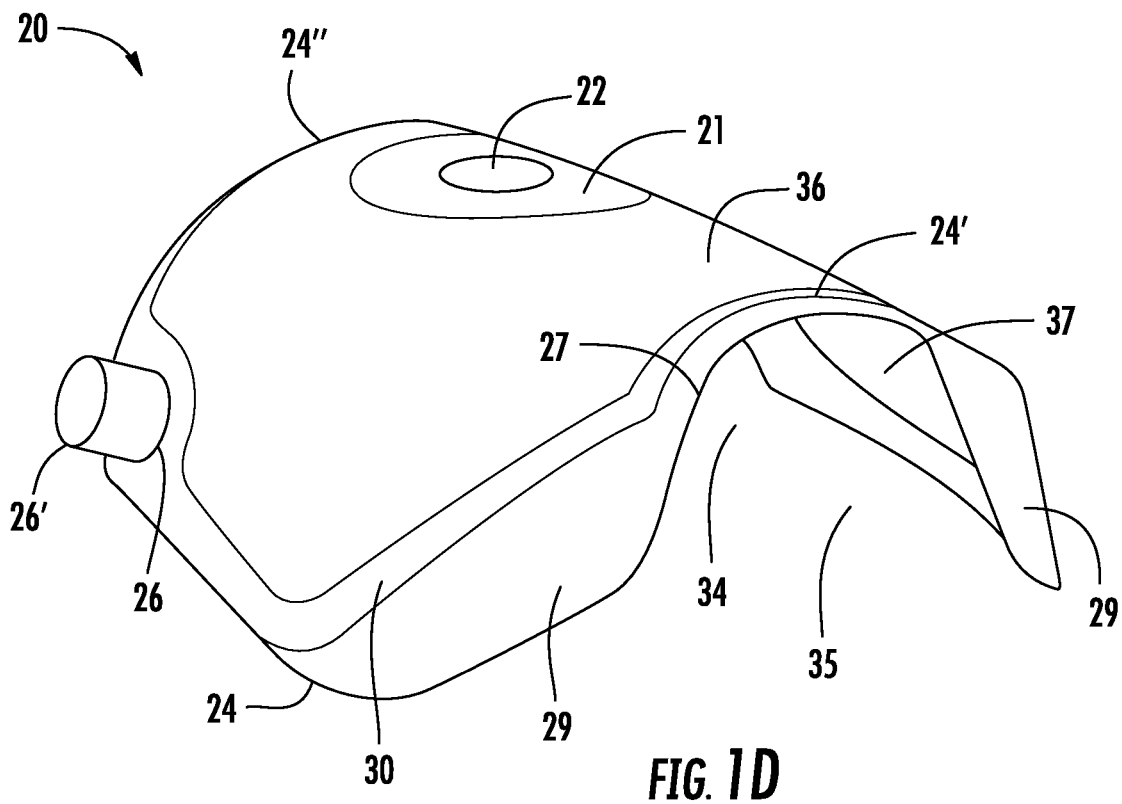
FIG. 1D is a perspective view of one embodiment of the shield assembly according to the present invention.
Figure 3:
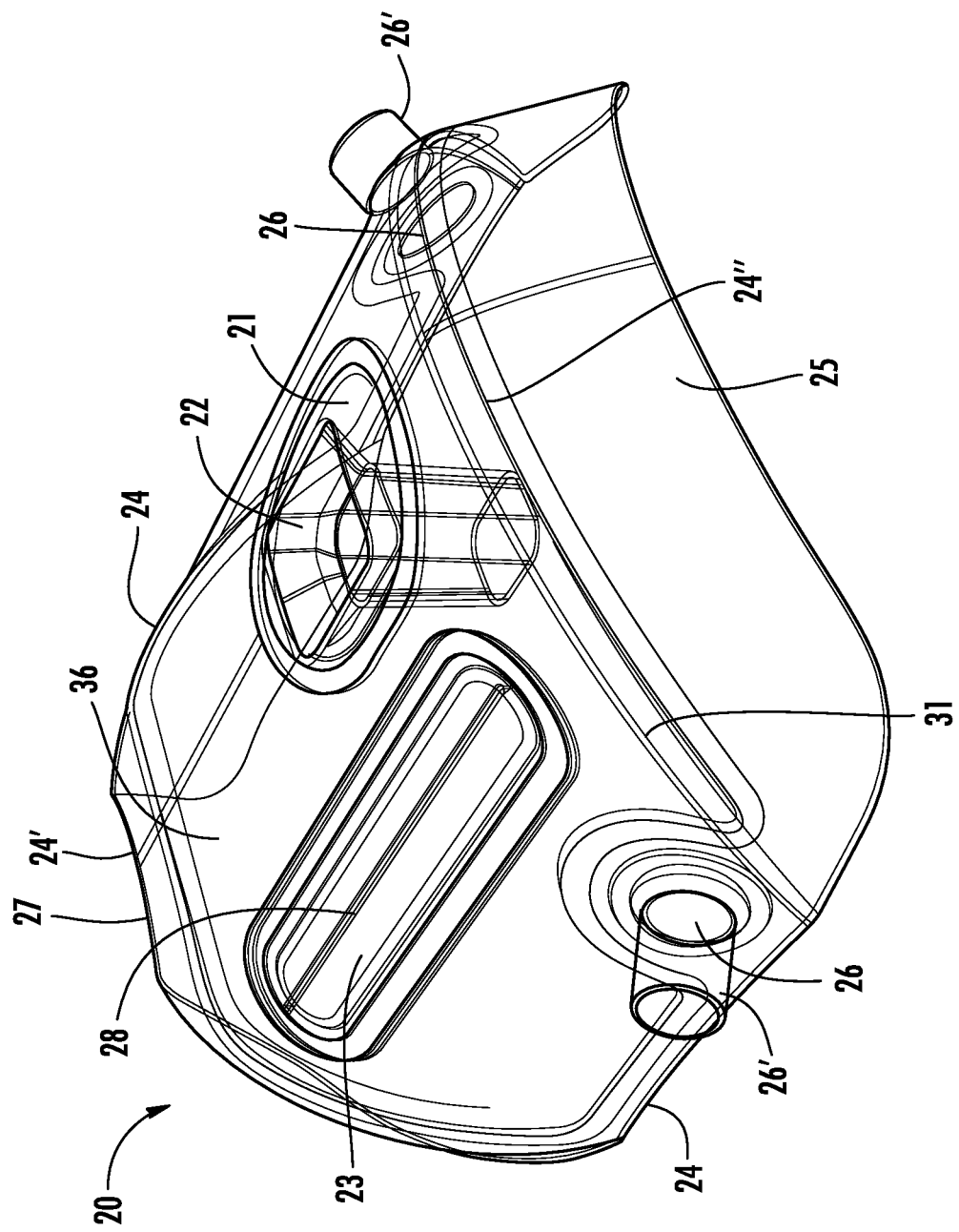
FIG. 3 is a perspective view of one embodiment of the shield assembly of the intubation assembly according to the present invention.

With reference now to at least FIG. 1D and FIG. 3, and as also referenced above, the present invention is directed towards an intubation assembly 1 comprising a shield assembly 20 as well as other embodiments comprising only the shield assembly 20. The shield assembly 20 comprises a body 24, which may comprise a plurality of side segments 29, which are shown on FIG. 1D. The shield body 24 may comprise a top surface 36 and a bottom surface 37 as well as proximal end 24' and a distal end 24". The shield body may comprise a variety of shapes and/or configurations, including, without limitation, a substantially arched configuration as is shown throughout the figures. However, this is not necessarily limiting as other shapes and/or configurations are also possible. The shield body 24 may primarily comprise a substantially transparent or translucent material. For example, the body 24, including the side segments 29 may primarily comprise a clear plastic. The material of the body 24 may comprise a rigid clear plastic. The material of the side segments 29 may potentially comprise a flexible material that may allow for further positioning adjustments 29 of the shield body and/or which may at least partially reduce the risk of injury to the patient, as for example, with the flexible material of the top portion 25. The shield assembly 20 may comprise a first transparent component 21, which is disposed substantially around the middle of the body 24. The first transparent component 21 may comprise a substantially transparent or translucent material. Further, the first transparent component 21 may also comprise a shield opening 22 for insertion of the intubation apparatus assembly 10. By way of example, the first transparent component 21 may comprise a clear silicone sheet with an opening disposed thereon. The shield assembly 20 may also comprise a second transparent component 23. The second transparent component may comprise a slot(s) 28 and enabling a fluid communication between the area above the top surface 36 of the shield body 24 and the area below the bottom surface of the shield body 37. It is within the scope of the present invention that the slot(s) 28 remain substantially closed unless the health practitioner selectively opens them, for example to insert an endotracheal tube, which will also be described in more detail later. As an example, the second transparent component 23 may comprise a clear silicone sheet a longitudinally disposed slot(s) 28.

Also with reference to at least the illustrative embodiment shown in FIG. 3, the shield assembly 20 of the intubation assembly 1 may comprise a top portion 25. The top portion 25 may be disposed on the distal end 24" of the shield body 24 and may comprise an elongated configuration. The top portion 25 may also comprise a substantially rounded or curved configuration. As shown at least in the illustrative embodiments of FIGS. 1A-1B and 3, the top portion 25 may be deposed at a downward inclination relative to the shield body 24. The top portion 25 may potentially comprise a flexible material to permit adjustments by the user and/or medical practitioner when positioning the shield body 24 on or around the patient, and/or to at least partially reduce the risk of injury to the patient, for example to the neck or chest area of the patient. As such, the top portion 25 as well as the bottom surface 37 of the shield body 24 may substantially define an enclosure are a 34, which is shown at least in FIG. 1D. The top portion 25 may also comprise a substantially soft or malleable material. For example, the top portion may comprise a soft silicone material. Furthermore, the top portion may comprise at least one vacuum opening 26. The vacuum opening 26 may be disposed in fluid communication with a vacuum connecting portion 26', which itself may be disposed in fluid communication with a vacuum tube. As such, a negative pressure may be transferred from the vacuum tube and/or system and exerted on the enclosure area 34. As shown in the illustrative embodiment of FIG. 3, two vacuum openings 26 may be provided. Further, a cap may be provided to cover one or both vacuum openings 26 and/or vacuum connecting portions 26". As an example, the vacuum openings 26 may comprise hose ports. The vacuum openings 26 may be operatively disposed with a vacuum system to provide negative pressure. As used herein, a "vacuum system" may refer to one or more components associated with vacuum equipment, including a vacuum tube or conduit that may exert a negative pressure, and/or other associated components, including, without limitation a vacuum machine and/or filtering apparatus. As such, and with reference to at least FIGS. 1A-1D and 3, one or more vacuum tubes may be operatively disposed on the vacuum openings 26 to enable a negative pressure on the side of the shield body 24 disposed against the face of the patient. As such, given the operative arrangement enabled by the geometry of the shield body 24 and vacuum openings 26, the resulting negative pressure should provide for an at least partially increased removal of exhaled infectious particles.

As is also shown at least in FIG. 1D, the shield assembly 20 may comprise a curvature 27. The curvature 27 may be substantially defined by the geometry of the ends of the side segments 29, which may for example comprise an elliptical configuration. The side segments 29 may be disposed on the proximal end 24' of the shield body 24, and further, may be disposed in a spaced apart relation to one another. As shown at least in FIG. 1D, the spaced apart relation between the side segments 29 may at least partially define an aperture 35. As such, the curvature 27 of the body 24 is advantageous to accommodate the arm of a health practitioner when holding the intubation apparatus assembly 10. Further, it is within the scope of the present invention that the curvature 27, the side segments 29, and/or the shield body 24, be configured and dimensioned to define an aperture 35 of a geometry and/or a sufficient dimension that may allow a user or practitioner to place his/her hand through the aperture 35 and into the enclosure area 34. As such, the user or practitioner may grab a sleeve 12 that has been inserted into the shield body 24.

Figure 4:
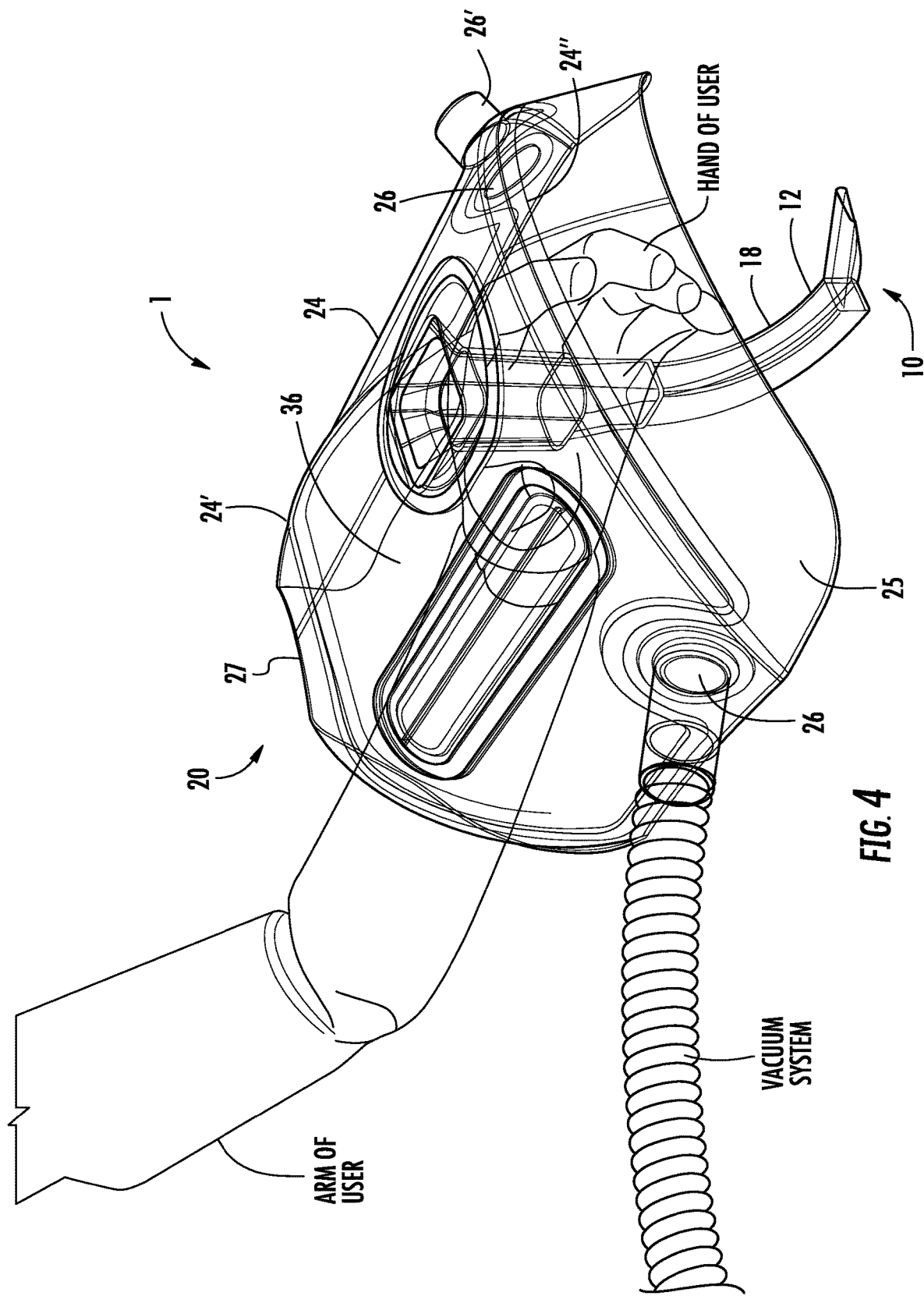
FIG. 4 is a perspective view of another embodiment of the shield assembly of the intubation assembly according to the present invention being operated by a user.

With reference now to FIGS. 1B and 4, and as mentioned above, it is within the scope of the present invention that the intubation apparatus assembly 10 be inserted into the sleeve opening 13 of the shield body 24. As such, a health practitioner may grab and/or position the intubation apparatus assembly 10 on an intended area of the body of the patient, e.g., the mouth, larynx, esophagus, and/or trachea. Because the diameter of the substantially circular configuration 13 of the sleeve 12 should be at least larger than the diameter of the shield opening 22, the sleeve 12 should be retained around its end on the first transparent component 212. However, the sleeve 12 should protrude on an opposite side of the shield body 24, i.e., the side facing the patient. As is perhaps best shown in FIG. 4, the sleeve 12 should remain movable with respect to the shield body 24 after insertion. However, the sleeve 12 should substantially pass through shield opening 22.

As is perhaps best shown in the illustrative embodiments of FIGS. 1A, 1B and 1D, the shield body 24 may comprise a sleeve retainer 32, which is shown in FIGS. 1A and 1B, and which is disposed on the bottom surface 37, which is shown in FIG. 1D. The sleeve retainer 32 is intended to act as a guide and/or support to the sleeve 12 once it has been inserted into the shield body 24. Accordingly the sleeve retainer 32 may be a channel or conduit which may extend below the shield opening 22 in a direction that is substantially perpendicular to the bottom surface 37. The sleeve retainer 32 should comprise an opening that corresponds to the shape of the shield opening 22 and/or sleeve 12, e.g., substantially square or substantially circular. The sleeve retainer 32 should allow for movement and/or adjustment of an inserted sleeve 12. For example, sleeve retainer 32 may be provided with four adjacently disposed walls to form a substantially square configuration extending away from the bottom surface 37. The sleeve retainer 32 may be provided with a recessed wall(s). That is, at least one of the adjacently disposed walls of the sleeve retainer 32 may comprise a lesser length that the other three to at least partially allow for movement and/or adjustment of the sleeve 12 in at least one direction. Additionally, an expandable component 33 may be provided along one or more of the walls to further allow for further movement and/or adjustment of the sleeve 12 in at least one direction, and in some embodiments in several directions. The expandable components 33 may comprise a corrugation or groove within the walls of the sleeve retainer 32, which may at least partially allow for such further movement and/or adjustment of the sleeve 12 once it has been inserted.

With reference now to at least FIGS. 1A-1D and 3, the shield assembly 20 may be provided with a reinforcement component 30 and/or an overlapping portion 31. A reinforcement component 30 and/or overlapping portion 31 may be provided to at least partially increase the stability of the shield body 24 and/or at least partially reduce bending of the shield body 24. As may be appreciated at least in FIG. 1D, the reinforcement component 30 may be disposed or otherwise formed on the top surface 36 of the shield body 24 around is proximal end 24'. The reinforcement component 30 may extend substantially along the width of the top surface 36 of the shield body. The reinforcement component 30 may comprise an elongated configuration and/or may follow or otherwise correspond to the profile of the curvature 27. The reinforcement component 30 may also be provided at an offset with respect to the curvature 27 and/or side segments 29. Conversely, and as may be appreciated at least in FIGS. 1A-1C and 3, the overlapping portion may be disposed or otherwise formed on the top surface 36 of the shield body 24 around its distal end 24". The overlapping portion 31 may be formed by an overlay or otherwise intersection between the shield body 24 and the top portion 25.

Figure 5:
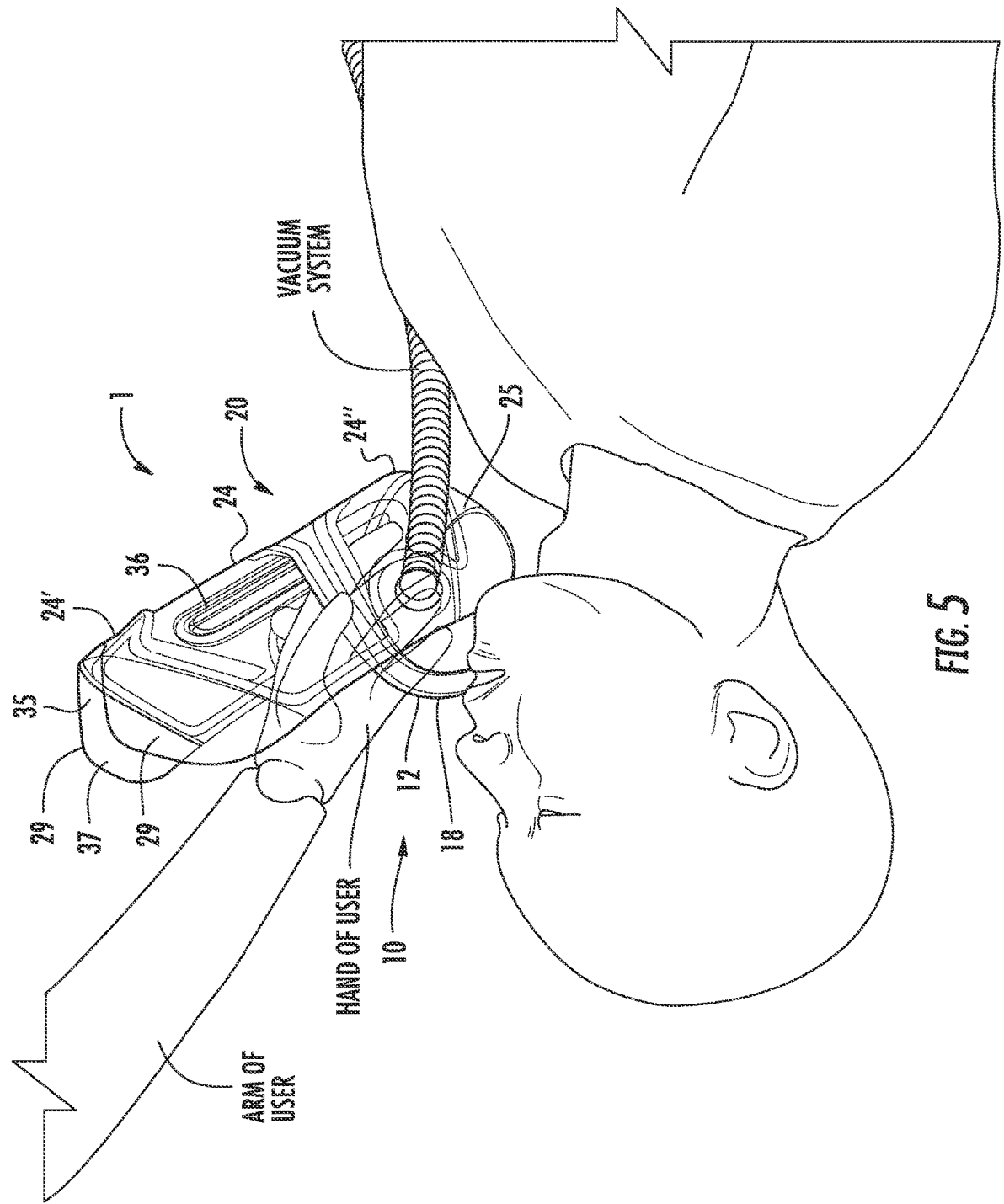
FIG. 5 is a side view of one embodiment of the shield assembly of the intubation assembly according to the present invention being operated by a user.
Figure 6:
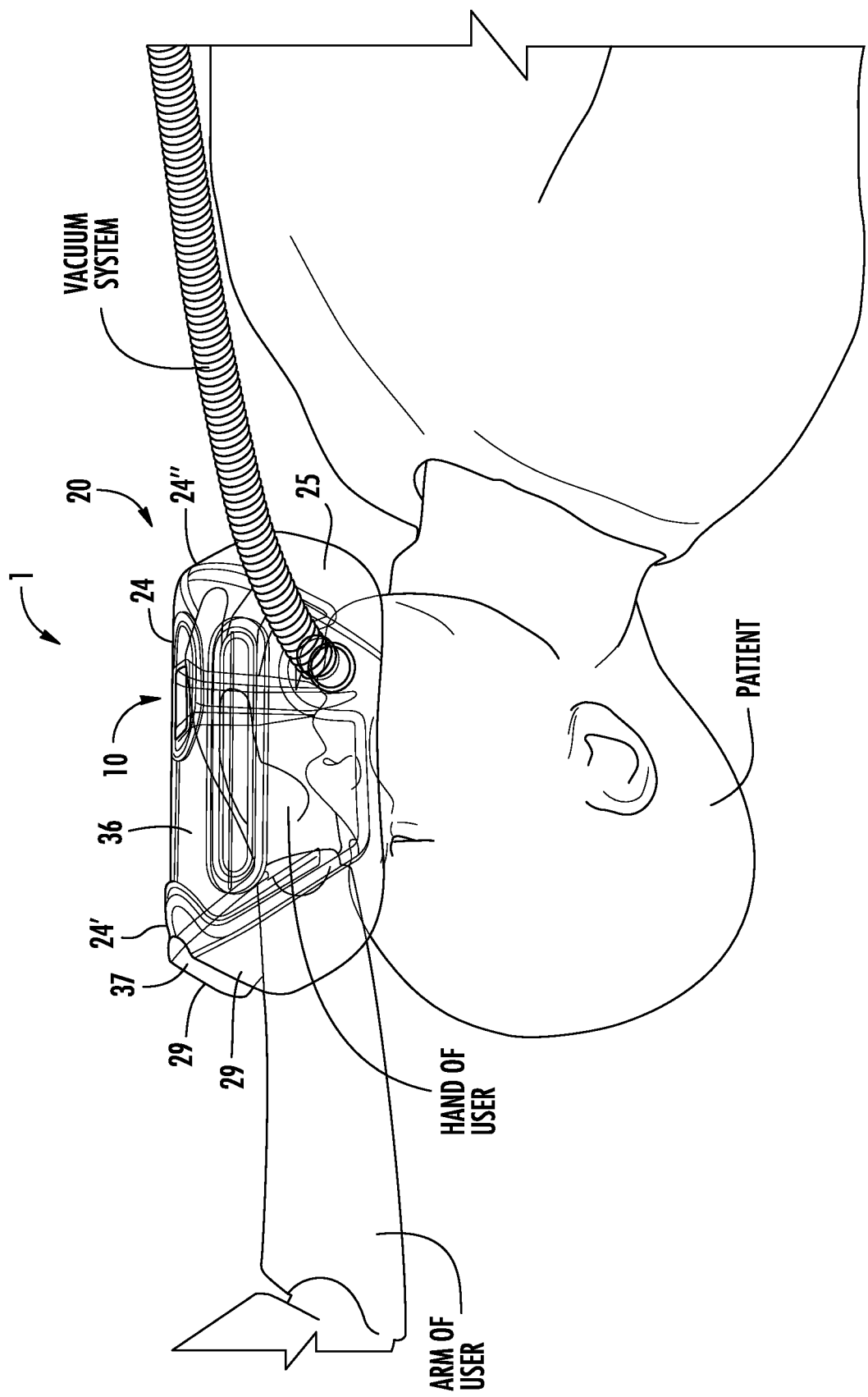
FIG. 6 is a side view of another embodiment of the shield assembly of the intubation assembly according to the present invention being operated by a user.

With reference now to FIGS. 4-8, features of the present invention comprise disposing the inventive intubation assembly 1 and/or shield assembly 20 into and out of an operative position and an inoperative position. As used herein, the "inoperative position" of the inventive intubation assembly 1 and/or shield assembly 20 refers the non-operation and/or storage of the various components of the intubation assembly 1 and/or shield assembly. The "inoperative position" may also refer to a position of the intubation assembly 1 and/or shield assembly 20 that does not involve placing the sleeve 12 into the shield body 24 or that does not involve dispose the shield assembly 20 being disposed in proximity to the face and/or head of the patient. Furthermore, the "inoperative position" may also refer to the non-operation of a vacuum system connected to the shield assembly 20 and/or shield body 24. With reference to FIG. 6, and as used herein, the "operative position" of the intubation assembly 1 and/or shield assembly generally comprises the intubation apparatus assembly 10, sleeve 12 and/or intubation apparatus, operatively disposed on the shield 24, i.e., inserted through the shield opening 22. The "operative position" also refers to the intubation apparatus assembly 10, sleeve 12 and/or intubation apparatus disposed in the mouth, larynx, esophagus, and/or trachea of the patient, which for simplicity may be collectively referred to as the mouth of the patient. The "operative position" may also refer to the shield body 24 disposed in proximity to the patient, and/or the bottom surface 37 facing the patient. Furthermore, the "operative position" may comprise the vacuum system connected to the vacuum opening 26 and/or vacuum connecting portion 26', and being disposed in an operational setting, i.e., exerting a negative pressure, such that a negative pressure is transferred to the enclosure area 34 and/or the area surrounding the patient. As such, at least partially exhaled air may be extracted from the area surrounding the patient, while the user or practitioner performs an intubation procedure.

Figure 7:
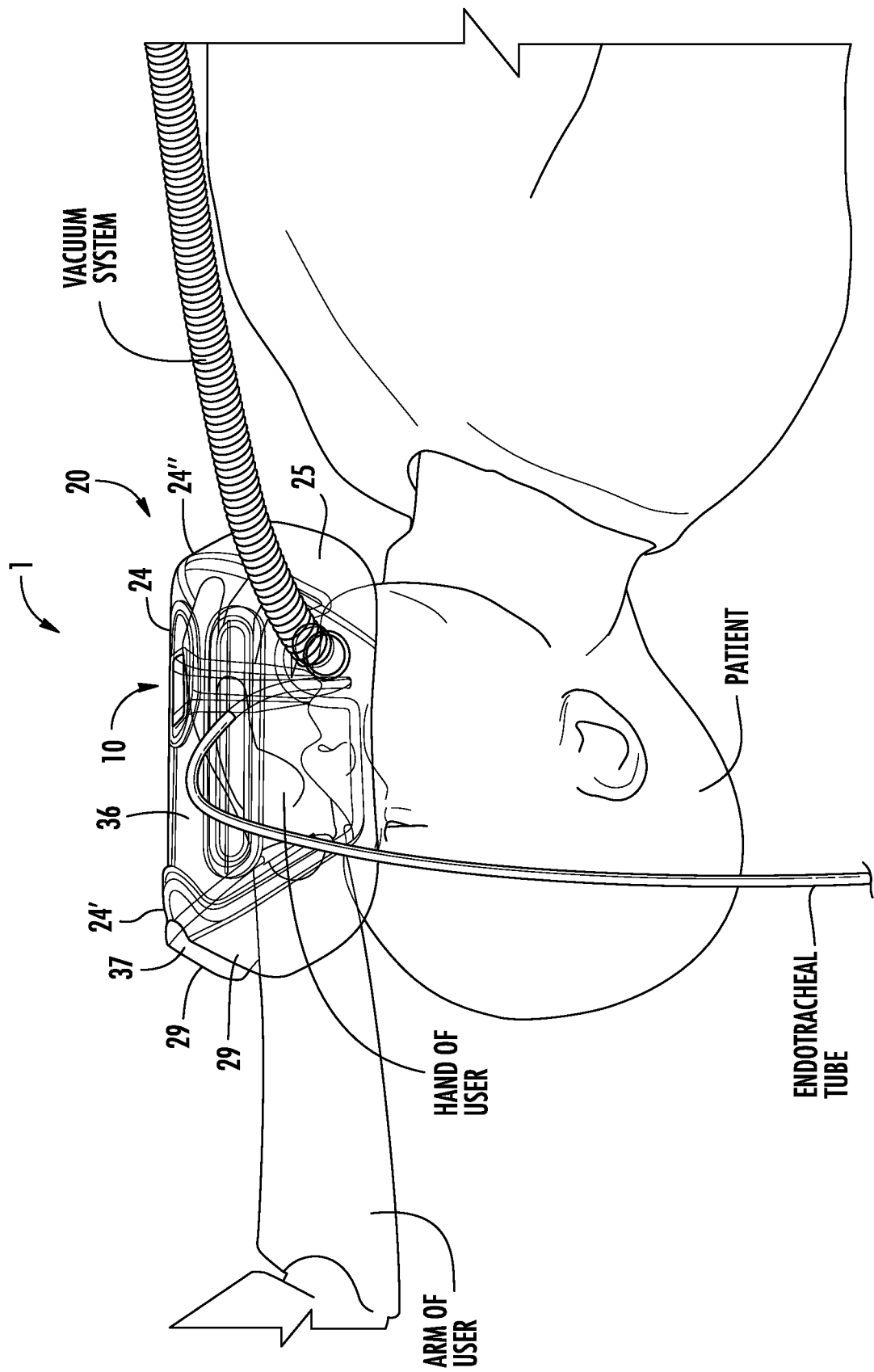
FIG. 7 is a side view of yet another embodiment of the shield assembly of the intubation assembly according to the present invention being operated by a user.
Figure 8:
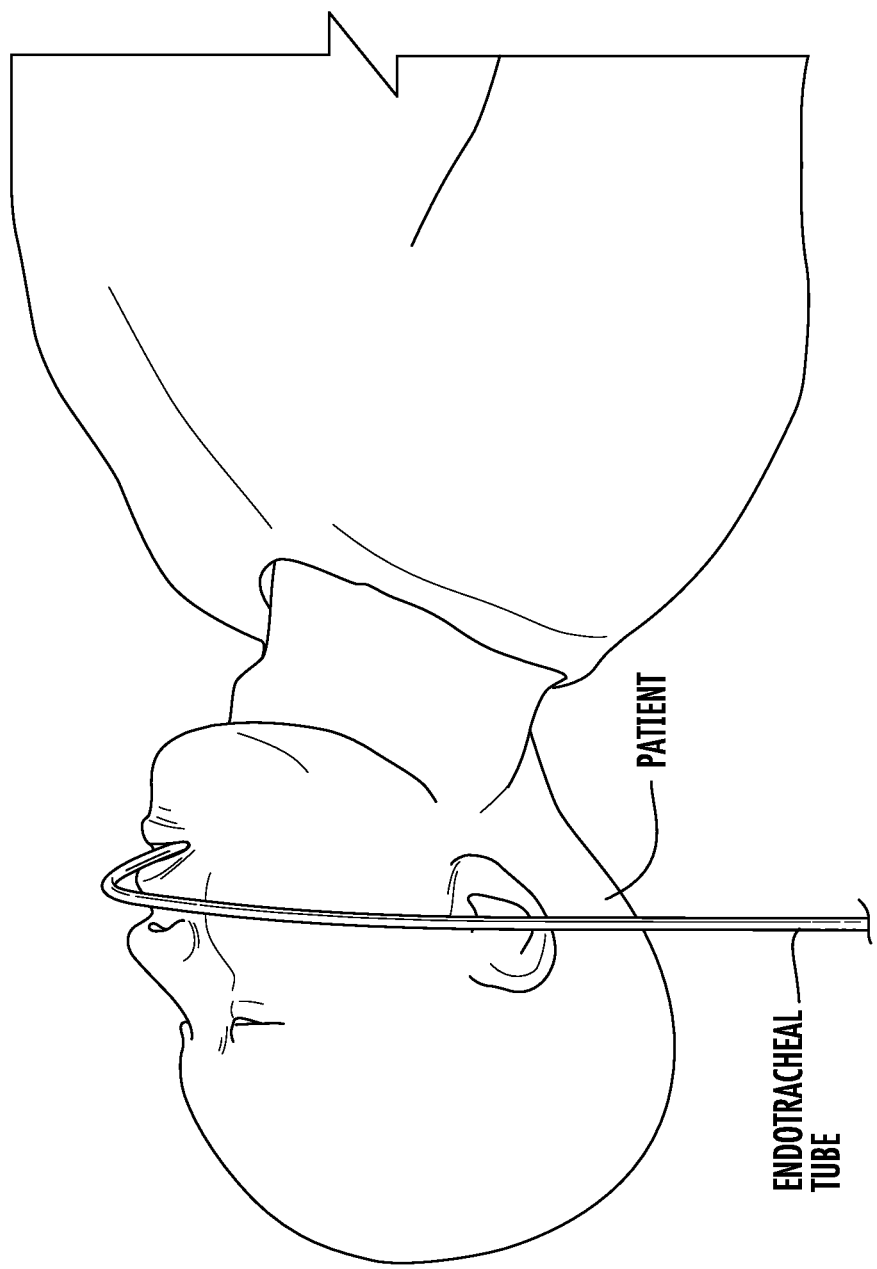
FIG. 8 is a side view of a patient intubated with the intubation assembly removed.

As shown in FIG. 5, the shield assembly 20, with the intubation apparatus assembly 10 and/or sleeve 12 inserted, may be positioned at a slight inclination with respect to the body of the patient. This at least partially facilitates an initial insertion of the sleeve 12 into the mouth of the patient. Here, the top portion 25 of the shield assembly 20 may come into contact with the neck of the patient. Accordingly, it is advantageous to provide a top portion 25 with a substantially soft material, e.g., soft silicone, to at least partially reduce the risk of physically injury, including around the neck of the patient. Once the sleeve 12 is initially inserted into the mouth of the patient, the shield assembly 20 may be manually moved from the position represented in FIG. 5 to the position represented in FIG. 6. During this process, the sleeve 12 may be inserted deeper into the mouth, and into the larynx, esophagus, and/or trachea of the patient. As shown in FIG. 7, once the shield assembly 20 and/or the intubation apparatus assembly 10 are disposed in an operative position, i.e., the position as represented in FIG. 6, an endotracheal tube may be passed through a slot 28 from an outside of the shield body 24 to the opposite side facing the patient. After being inserted through the at least one of the slots 28, the endotracheal tube may be placed on mouth of the patient. Thereafter, the endotracheal tube may be selectively positioned on an intended area of the patient, for example, an intended location of the larynx and/or trachea. At this stage, the audiovisual component 19 may assist the health practitioner in positioning the endotracheal tube on the intended area of the patient. As shown in FIG. 8, after the endotracheal tube has been inserted and/or positioned on an intended area of the patient, the shield assembly 20 and intubation apparatus assembly 10 may be removed.

Figure 9:
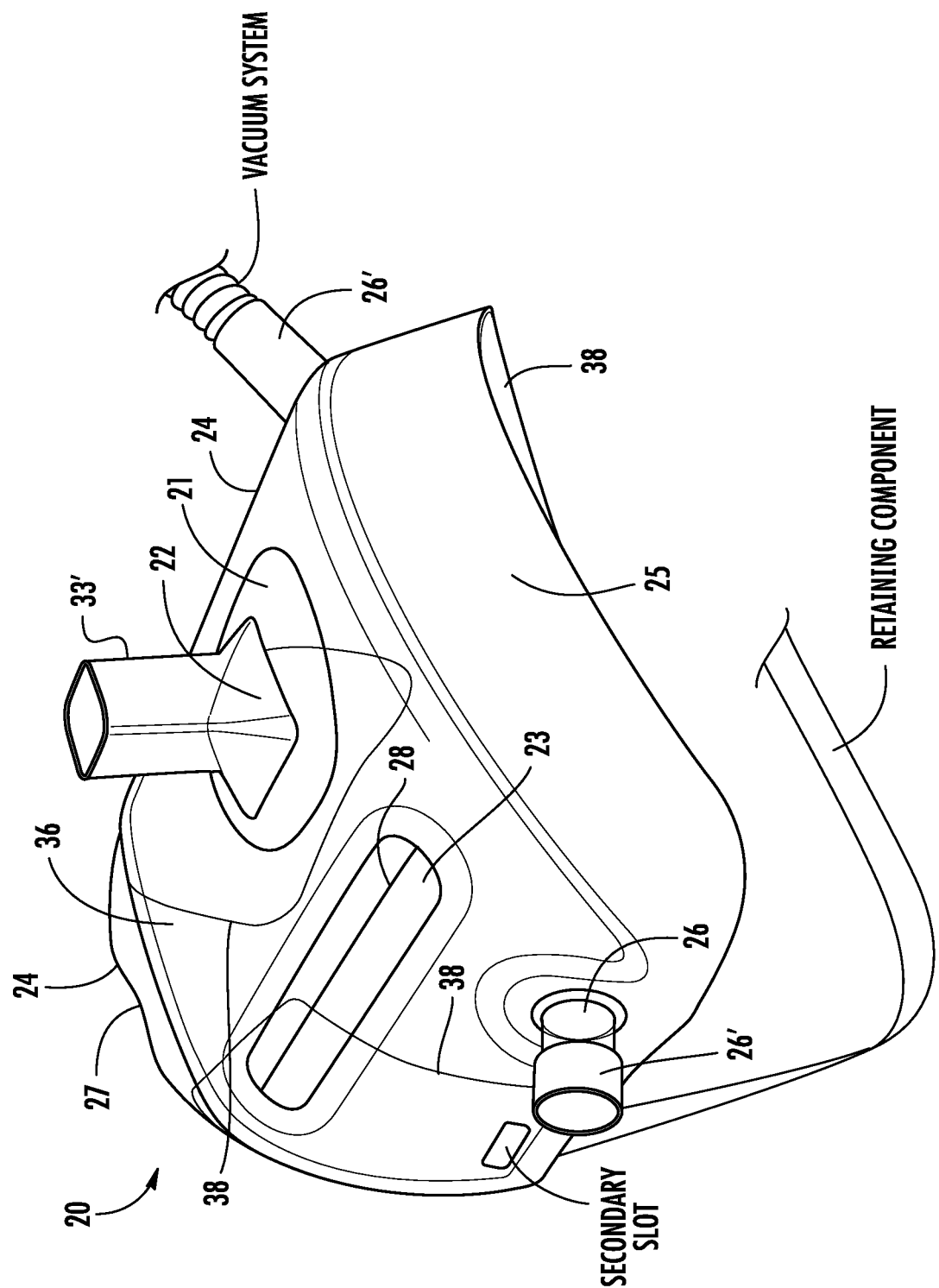
FIG. 9 is a perspective view of one embodiment of the shield assembly of the intubation assembly according to the present invention comprising offset structures.
Figure 10:
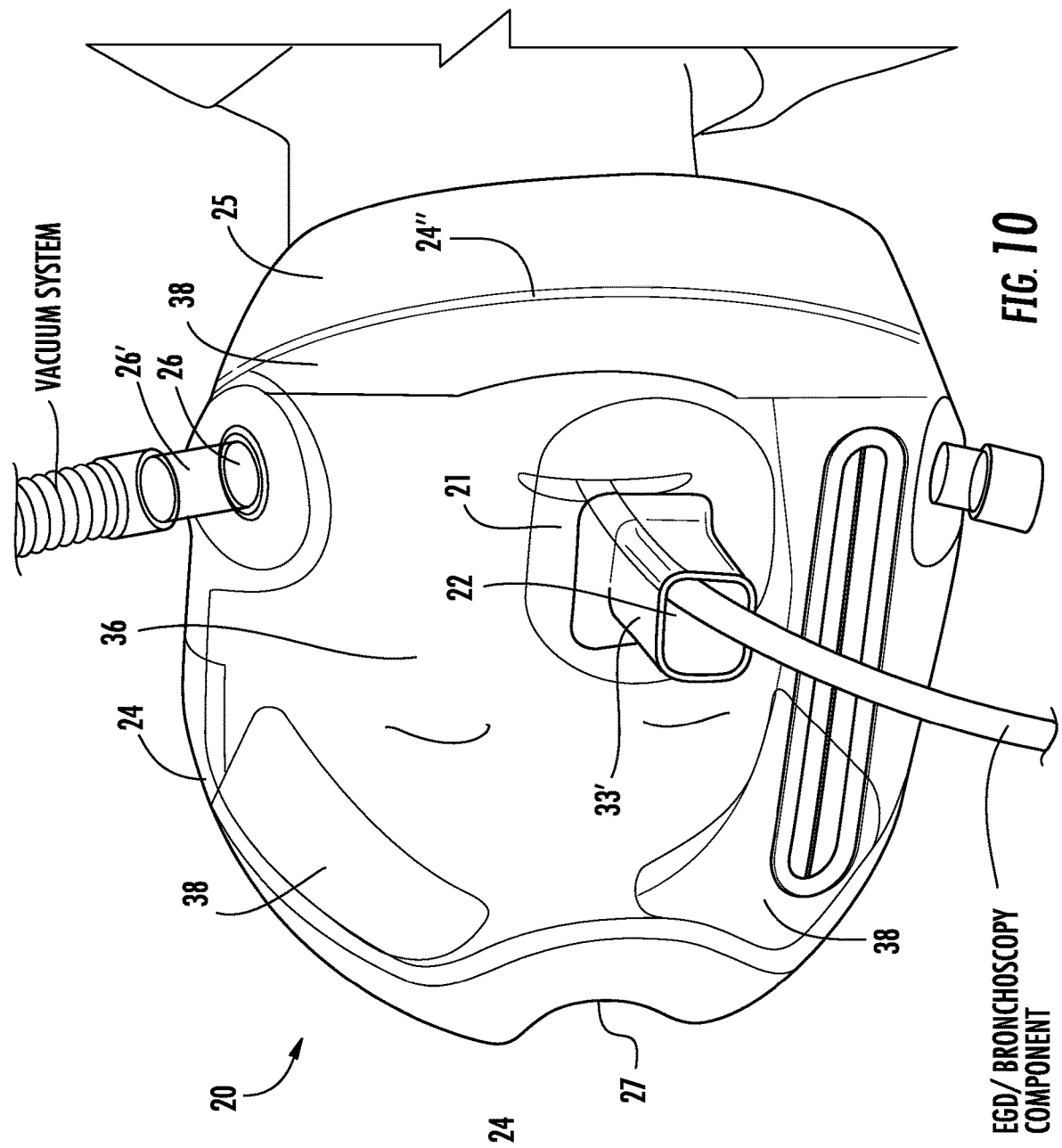
FIG. 10 is a front view of one embodiment of the shield assembly of the intubation assembly according to the present invention comprising offset structures and being operatively disposed on the head of a patient.

With reference to FIGS. 9-10, additional features of the present invention comprise providing a shield assembly 20 with an offset structure 38. In some applications, it may be of interest that the shield body 24 be connected to the head of the patient, to at least partially limit movement of the shield 24 with respect to the body of the patient. For example, during an upper GI endoscopy (EGD) and/or a bronchoscopy, a retaining component, i.e., adjustable straps, ties, bands, etc., may be provided to dispose the shield body 24 around the head of the patient. The retaining component should at least partially reduce movement of the shield body 24 with respect to the body of the patient. The retaining component may be connected to the shield body around a secondary slot or opening configured and dimensioned for the size of the retaining component. For such applications, e.g., an upper GI endoscopy (EGD), a bronchoscopy and/or a related procedure, a shield body 20 may be provided with an offset structure 38, which is primarily intended to provide for a separation between the shield body 24 and the body of the patient, inducing the head, forehead, face, neck, upper portion of the chest, and/or shoulders, etc. It is within the scope of the present invention that such separation between the body and the offset structure 38 may be beneficial to at least partially protect the areas of the patient that may otherwise be in direct contact with the shield body 24, e.g., head, forehead, face, neck, upper portion of the chest, and/or shoulders. Accordingly, an offset structure 38 may be provided around the bottom surface 37 of the shield body 24.

As seen in FIGS. 9-10, the offset structure 38 may be provided around the bottom surface 37 of the shield body 24, including around the top portion 25 and/or the side segments 29. By way of example only, the offset structure 38 may comprise a foam pillow liner or other related material, e.g., a foam pad, such that it may serve to elevate or otherwise raise the position of the shield body 24 with respect to the body of the patient. As such, once the shield body 24 is disposed on the head of the patient, the intubation apparatus, e.g., bronchoscope and/or endoscope, may be inserted through the shield opening 22. In such embodiments, it is further contemplated that the vacuum opening(s) 26 and/or vacuum connecting portion(s) 26 also operate as described herein, to at least partially remove exhaled air from the patient with an operatively connected vacuum system. In such embodiments, and in addition to, or in lieu of, the offset structure(s) 38, a retainer 33' may be provided. The retainer 33' may be oriented outwards, i.e., away from the top surface 36, instead of inwards, i.e., away from the bottom surface 37 and/or towards the patient. A retainer 33' may be provided to further assist the user or practitioner to insert the intubation apparatus, e.g., EGD apparatus, bronchoscope and/or other related apparatus may be inserted through a retainer 33' disposed around the shield opening 22. As with the sleeve retainer 33, the retainer 33' is intended to function as a guide for the intubation apparatus.

With reference now to FIG. 11, the present invention is further directed to a method 100 of using the inventive intubation assembly 1. As shown at 110, the method 100 initially comprises providing an intubation assembly 1 comprising an intubation apparatus assembly 10 and a shield assembly 20 as described herein. As shown at 120, the method 100 further comprises placing an intubation apparatus into a sleeve 12 of the intubation apparatus assembly 10 of the inventive intubation assembly 1. As shown at 130, the method 100 further comprises inserting the sleeve 12 through the opening 22 of the shield body 24. As shown at 140, the method 100 further comprises inserting a hand of a user into the enclosure area 34 and grabbing the sleeve 12. As shown at 150, the method 100 further comprises positioning the sleeve 12 into the mouth of the patient. It should be understood that once the sleeve 12 is positioned into the mouth of the patient, that the shield body 24 will at least partially surround the face and/or head of the patient, and that the bottom surface 37 of the shield body 24 should face the patient. As shown at 160 the method 100 further comprises disposing the shield 24 assembly and the intubation apparatus assembly into the operative position.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A shield assembly structured for insertion of an intubation apparatus and configured to at least partially reduce displacement of exhaled particles from a patient, said shield assembly comprising:
   a shield body comprising a top surface and a bottom surface,
   the shield body having a length adapted to extend at least from the patient's chin to the patient's eyes,
   a top portion disposed on a distal end of said shield body,
   a first side segment and a second side segment, each one of said first side segment and said second side segment disposed on a proximal end of said shield body, said first side segment and said second side segment being disposed in spaced apart relation to one another collectively defining an aperture, said aperture being configured and dimensioned to allow access to a hand and arm of a user to an enclosure area and make positional adjustments of the shield body with respect to a front side of the patient,
   said top portion and said bottom surface of said shield body collectively defining said enclosure area,
   said shield body comprising an opening structured and dimensioned for insertion of the intubation apparatus,
   at least one vacuum opening disposed on said shield body and structured for attachment to a vacuum tube,
   said shield body disposable into and out of an operative position and an inoperative position, and
   said operative position comprising the intubation apparatus being disposed on said shield opening and extending into the mouth of the patient; an interior of said shield body oriented to face the front side of the patient, and
   the shield body not configured to extend along the patient's ears in the operative position.

2. The shield assembly as recited in claim 1 wherein said first side segment, said second side segment and said shield body collectively define a curvature around said aperture.

3. The shield assembly as recited in claim 2 further comprising a reinforcement structure disposed around said proximal end of said shield body; said reinforcement structure configured to at least partially reduce bending of said shield body.

4. The shield assembly as recited in claim 3 wherein said reinforcement structure comprises a profile structured to correspond to said curvature around said aperture.

5. The shield assembly as recited in claim 1 further comprising an overlapping portion formed around said distal end of said shield body; said overlapping portion configured to at least partially reduce bending of said shield body.

6. The shield assembly as recited in claim 5 wherein said overlapping portion is at least partially defined by an overlay of said shield body and said top portion.

7. The shield assembly as recited in claim 1 wherein further comprising a reinforcement structure disposed around said proximal end of said shield body; said reinforcement structure configured to at least partially reduce bending of said shield body.

8. The shield assembly as recited in claim 1 further comprising a vacuum connecting portion disposed around said at least one vacuum opening; said vacuum connecting portion configured and dimensioned for attachment to the vacuum tube.

9. The shield assembly as recited in claim 8 wherein said operative position comprises the vacuum tube exerting a negative pressure around the enclosure area and adapted to at least partially remove exhaled air from the patient around the space between said shield body and the front side of the patient.

10. The shield assembly as recited in claim 1 further comprising at least one slot structured to allow an insertion of an endotracheal tube into said enclosure area.

11. The shield assembly as recited in claim 1 wherein said shield body comprises a substantially arched configuration.

12. The shield assembly as recited in claim 1 wherein said top portion comprises a flexible material.

13. The shield assembly as recited in claim 1 wherein each of said first side segment and said second side segment comprise a flexible material.

14. The shield assembly as recited in claim 1 further comprising an offset structure is disposed on said bottom surface of said shield body; said offset structure configured to at least partially provide a separation between said shield body and the patient.

15. The shield assembly as recited in claim 14 wherein said offset structure is at least partially disposed around said top portion of said shield body.

16. The shield assembly as recited in claim 14 wherein said offset structure is at least partially disposed around each one of said first side segment and said second side segment.

17. An intubation assembly structured for insertion of an intubation apparatus and configured to at least partially reduce displacement of exhaled particles from a patient, said intubation assembly comprising:
   an intubation apparatus assembly comprising a sleeve, said sleeve configured and dimensioned to receive an intubation apparatus on an inside thereof, said sleeve further configured and dimensioned for insertion into the mouth of the patient,
   shield body comprising a top surface and a bottom surface,
   the shield body having a length adapted to extend at least from the patient's chin to the patient's eyes,
   a top portion disposed on a distal end of said shield body,
   a first side segment and a second side segment, each one of said first side segment and said second side segment disposed on a proximal end of said shield body,
   said first side segment and said second side segment being disposed in spaced apart relation to one another collectively defining an aperture, said aperture being configured and dimensioned to allow access to a hand and arm of a user to an enclosure area and said sleeve,
   said top portion and said bottom surface of said shield body collectively defining said enclosure area, said shield body comprising an opening for insertion of said sleeve, at least one vacuum opening disposed on said shield body and structured for attachment to a vacuum tube, said shield body and said sleeve collectively disposable into and out of an operative position and an inoperative position, said operative position comprising the intubation apparatus being disposed on said shield opening and extending into the mouth of the patient; an interior of said shield body oriented to face a front side of the patient, and said aperture further configured and dimensioned to allow the hand of the user to retain the sleeve and make manual positional adjustments of the shield body with respect to the front side of the patient when said shield body and said sleeve are disposed in said operative position, and the shield body not configured to extend along the patient's ears in the operative position.

18. The intubation assembly as recited in claim 17 wherein said sleeve comprises a body configured and dimensioned to correspond to a body of the intubation apparatus.

19. The intubation assembly as recited in claim 17 wherein said intubation apparatus assembly comprises an audiovisual component.

20. The intubation assembly as recited in claim 17 wherein said shield body comprises a sleeve retainer disposed on said bottom surface; said sleeve retainer configured and dimensioned to orient said sleeve into the mouth of the patient.

21. The intubation assembly as recited in claim 20 wherein said sleeve retainer comprises at least one expandable component; said at least one expandable component defined along the length of said sleeve retainer and structured to at least partially allow for movement of said sleeve within said shield body.

22. A method of using an intubation assembly to at least partially reduce displacement particles from a patient, the method comprising:

providing an intubation shield assembly comprising:

an intubation apparatus assembly comprising a sleeve, the sleeve configured and dimensioned to receive an intubation apparatus on an inside thereof, the sleeve further structured and dimensioned for insertion into the mouth of the patient, a shield body comprising a top surface and a bottom surface, the shield body having a length adapted to extend at least from the patient's chin to the patient's eyes, a top portion disposed on a distal end of the shield body, a first side segment and a second side segment, each one of the first side segment and the second side segment disposed on a proximal end of the shield body, the first side segment and the second side segment being disposed in spaced apart relation to one another collectively defining an aperture, the aperture being configured and dimensioned to allow access to a hand and arm of a user to an enclosure area, the top portion and the bottom surface of the shield body collectively defining the enclosure area, the shield body comprising an opening for insertion of the sleeve, at least one vacuum opening disposed on the shield body and structured for attachment to a vacuum tube, and the shield body and the sleeve collectively disposable into and out of an operative position and an inoperative position, the operative position comprising the intubation apparatus being disposed on the shield opening and extending into the mouth of the patient; an interior of the shield body oriented to face a front side of the patient, the aperture being further configured and dimensioned to allow the hand of the user to make manual positional adjustments of the shield body with respect to the front side of the patient and of the sleeve with respect to the mouth of the patient, when the shield body and the sleeve are disposed in the operative position, and the shield body not configured to extend along the patient's ears in the operative position, placing an intubation apparatus into the sleeve, inserting the sleeve through the opening of the shield body, inserting a hand of a user into the enclosure area and grabbing the sleeve, positioning the sleeve into the mouth of the patient, disposing the shield assembly and the intubation apparatus assembly into the operative position.

23. The intubation assembly as recited in claim 17 wherein said aperture is further configured and dimensioned to allow the hand of the user to retain the sleeve and manually insert it into the mouth of the patient when said shield body and said sleeve are disposed in said operative position.

24. An intubation assembly structured for insertion of an intubation apparatus and configured to at least partially reduce displacement of exhaled particles from a patient in a non-airtight environment, said intubation assembly comprising:

an intubation apparatus assembly comprising a sleeve, said sleeve configured and dimensioned to receive an intubation apparatus on an inside thereof, said sleeve further configured and dimensioned for insertion into the mouth of the patient, a shield body comprising a top surface and a bottom surface, the shield body having a length adapted to extend at least from the patient's chin to the patient's eyes, a top portion disposed on a distal end of said shield body, a first side segment and a second side segment, each one of said first side segment and said second side segment disposed on a proximal end of said shield body, said first side segment and said second side segment being disposed in spaced apart relation to one another collectively defining an aperture, said aperture being configured and dimensioned to allow access to a hand and arm of a user to an enclosure area and said sleeve, said top portion and said bottom surface of said shield body collectively defining said enclosure area, said shield body comprising an opening for insertion of said sleeve, at least one vacuum opening disposed on said shield body and structured for attachment to a vacuum tube, said shield body and said sleeve collectively disposable into and out of an operative position and an inoperative position, said operative position comprising the intubation apparatus being disposed on said shield opening and extending into the mouth of the patient; an interior of said shield body oriented to face a front side of the patient, and said aperture further configured and dimensioned to allow the hand of the user to retain the sleeve and manually insert it into the mouth of the patient and make manual positional adjustments of the shield body with respect to the front side of the patient and of said sleeve and said intubation apparatus with respect to the mouth of the patient, when said shield body and said sleeve are disposed in said operative position, and the shield body not configured to extend along the patient's ears in the operative position.

\* \* \* \* \*